United States Patent [19]

Bardos et al.

[11] Patent Number: 4,617,398

[45] Date of Patent: Oct. 14, 1986

[54] PHOSPHOAZIRIDINE COMPOUNDS USEFUL FOR TREATMENT OF TUMORS

[75] Inventors: Thomas J. Bardos, Snyder; Michael E. Perlman, Amherst, both of N.Y.

[73] Assignee: The Research Foundation of State University of New York, Albany, N.Y.

[21] Appl. No.: 367,338

[22] Filed: Apr. 12, 1982

[51] Int. Cl.$^4$ .................. C07D 403/02; C07D 403/14; A61K 31/395

[52] U.S. Cl. .................................... 548/112; 514/83; 548/956

[58] Field of Search ................. 260/239 EP; 424/200; 548/335, 112

[56] References Cited

U.S. PATENT DOCUMENTS

| 2,606,900 | 8/1952 | Parker et al. | 260/239 EP |
| 3,201,313 | 8/1965 | Bardos et al. | 424/200 |
| 3,314,848 | 4/1967 | Ratz et al. | 424/200 |
| 3,865,830 | 2/1975 | Turkevich et al. | 260/239 EP |

OTHER PUBLICATIONS

Burger ed., Medicinal Chemistry 3rd ed., Wiley-Interscience, N.Y., 1970, pp. 694–697.
Wodinsky et al., Chem. Abstracts, 92:121773n.
Wampler et al., Absence of Cross-Resistance to Alkylating Agents in Cyclophosphamide-Resistant L1210 Leukemia, Europ. J. Cancer, vol. 14, pp. 977–982, 1978.
Bardos et al., Synthesis of Potential Dual Antagonists III, Jour. of Pharmaceutical Sciences, vol. 54, No. 2, Feb., 1965.
Chmielewicz et al., Synthesis and Chemotherapeutic Effects of Ethyl Bis-(2,2-Dimethyl)-Ethylenamido Phosphate. A Preliminary Report, Jour. of Pharmaceutical Sciences, vol. 56, No. 9, Sep. 1967.
Wodinsky et al., Combined Therapy with an Aziridine Derivative NSC 200724 (AB182) and Radiation on an Experimental Leukemia. Int. J. Radiation Oncology Biol. Phys., vol. 4, pp. 1677–1680, 1979.
Hsiao et al., Synthesis of New Bis(1-Aziridinyl) Phosphinate Alkylating Agents Containing O-Phenyl N-Phenylcarbamate Side Chains, Jour. of Med. Chem, vol. 16, p. 391, 1973.
Lalka et al., Reactions of 2,2-Dimethyl-Aziridine-Type Alkylating Agents in Biological Systems I: Colorimetric Estimation and Stability in Physiological Media, Jour. of Pharmaceutical Sciences, vol. 62, No. 8, Aug., 1973.
Bardos et al., Synthesis of Potential Dual Antagonists IV, Jour. of Pharmaceutical Sciences, Vol. 54, No. 3, Mar., 1965.
Hsiao et al., Synthesis of Bis(Aziridinyl)Phosphinyl-N-Hydroxyurethane Derivatives as Antineoplastic Agents, Jour. of Medical Chemistry, vol. 18, p. 195, 1975.
Bardos et al., Combination of Chemotherapy with Dual Antagonists and Radiotherapy in the Treatment of Neoplastic Disease, Journal of Surgical Oncology 3(4); pp. 431–441, 1971.
Bardos et al., Structure–Activity Relationships of Alkylating Agents in Cancer Chemotherapy, Annals of The New York Academy of Sciences, vol. 163, Article 2, pp. 1006–1025, Oct. 3, 1969.
Chmielwicz et al., Alternations of Some Macromolecular and Biochemical Properties of Calf Thymus DNA Caused by "Dual Antagonists" and Nitrogen Mustard, Cancer Research, 27, pp. 1248–1257, Jul. 1967.
Munson et al., Preparation and Antitumor Activity of Tris(2,2-Dimethyl-1-Aziridinyl)Phosphine Oxide (TEPA-132), Cancer Chemotherapy Reports, vol. 51, No. 5. pp. 253–259, Sep. 1967.
Bardos et al., Effects of Ring-C-Methyl Substituents on the Chemical and Biological Activities of Ethylenimine Type Alkylating Agents Int. Congress of Chemotherapy, Jun. 1967.

(List continued on next page.)

Primary Examiner—Donald G. Daus
Assistant Examiner—William A. Teoli, Jr.
Attorney, Agent, or Firm—William J. Crossetta; Michael L. Dunn

[57] ABSTRACT

Novel phosphoaziridines of the formula:

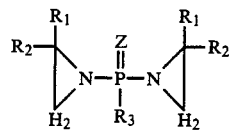

wherein Z is oxygen or sulfur, $R_1$ is independently at each occurrence H or —$CH_3$, $R_2$ is independently at each occurrence —$CH_3$ or nitrophenyl $R_5$; $R_3$ is —$NHR_4$, —$OR_4$, —$SR_4$ or

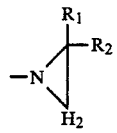

where $R_4$ is a radical containing up to 30 atoms including at least one amine, ester, ether, alkyl, substituted alkyl, hydrogen, phenyl, substituted phenyl, carbamate, heterocyclic ring or $R_5$ group; provided that, when $R_4$ contains and $R_5$ group, $R_4$ has an alkyl group between the phosphorous and the $R_5$ group; and $R_5$ is a radical containing and electron affinic group comprising a quinone, or a heterocyclic or phenyl ring directly connected to a radical selected from the group consisting of nitro, nitroso, sulfinyl, sulfoxine, and N-oxide; provided that the compound contains at least one $R_5$ radical and provided that when $R_1$ is H, the $R_2$ group on the same ring is $R_5$; and the method for using the above compounds for the treatment of tumors.

8 Claims, No Drawings

OTHER PUBLICATIONS

Bardos, Antimetabolites, Molecular Design and Mode of Action, Topics in Current Chemistry, vol. 52, pp. 90 and 91 only, 1974.

Lalka et al., Cyclophosphamide, 2,2-Dimethyl-Aziridines and Other Alkylating Agents as Inhibitors of Serum Cholinesterase, Biochemical Pharmacology, vol. 24, pp. 455-462, 1975.

Lalka et al., Reactions of 2,2-Dimethyl-Aziridine-Type Alkylating Agents in Biological Systems II: Comparative Pharmacokinetics in DOGS, Jour., of Pharmaceutical Sciences, vol. 64, No. 2, Feb., 1975.

Bardos et al., Chemical Mechanism of the Radiation Potentiating Effects of 2,2-Dimethylaziridine-Type Antitumor Agents, Int. J. Radiation Oncology Biol. Phys., vol. 4, pp. 1653-1656, 1979.

Wampler et al., Radiation Potentiating Effect of Ethyl Bis(2,2-Dimethyl-1-Aziridinyl) Phosphinate (AB-163), Int. J. Radiation Oncology Biol. Phys., vol. 5, pp. 1681-1683, 1979.

Hsiao et al., Synthesis of 5'-Thymidinyl Bis(-1-Aziridinyl)Phosphinates as Antineoplastic Agents, Jour of Med. Chemistry, vol. 24, pp. 887-889, 1981.

Zhdanov et al., Biologically Active Stable Radicals; XV[1]. Spinlabeled Alkyl Carbamate-N-Phosphonic Acid Aziridides, "Synthesis" pp. 269-271, 1979.

Konieczny et al., Methods for the Preparation of Spin-Labeled Phosphorus Compounds and Applications of Some of Them to Phosphorylative Spin-Labeling, "Synthesis", Sep. 1981.

Kimler et al., Development and Testing of New Hypoxic Cell Radiosensitizers, Radiology, vol. 33, pp. 515-517, 1979.

PHOSPHOAZIRIDINE COMPOUNDS USEFUL FOR TREATMENT OF TUMORS

TECHNICAL FIELD

This invention relates to phosphoraziridine compositions and to their use as antineoplastic agents. The invention more particularly relates to novel phosphoraziridine compositions and their use in controlling leukemia and tumors. The compositions also find utility as antibacterials and certain of the compositions may find utility as other pesticides such as fungicides, nematocides and other antimicrobials.

BACKGROUND ART

Cancer is a general term used when referring to any disease state that results from an abnormal uncontrolled and progressive cellular growth. There are presently three major methods available for the treatment of cancer. These methods are surgery, radiotherapy and chemotherapy. Each method of treatment may be effective by itself; however, when administered in combination, the results are frequently more favorable. A common example of such a combination would be the utilization of surgery to remove a tumor followed by treatment with certain chemicals capable of controlling or eliminating remaining cells which may move through the body to seed the growth of additional tumor sites (metastasis).

Unfortunately, such treatment with chemicals (chemotherapy) continues to have very serious disadvantages. In particular, none of the approximately 30 drugs commonly used in cancer chemotherapy have proven to be capable of eliminating the cancer disease except in a relatively small number of isolated cases. Furthermore, most of these chemicals have very high toxicity or serious side effects relative to the dosage required to be effective against the abnormal tumor or growth (neoplasm). The use of such chemicals in chemotherapy therefore very often results in serious complications which endanger the human being or other host organism being treated. These disadvantages of cancer treating chemicals (antineoplastic drugs) continue despite the fact that many thousands of potential antineoplastic agents have been screened and tested.

Many of the effective antineoplastic agents are classified as alkylating agents, i.e. a substance which introduces an alkyl, or substituted alkyl radical into a compound in place of a hydrogen atom. In chemicals utilized for treating cancer such alkylation frequently occurs within a nucleic acid structure such as DNA or RNA of the cancer cell thus effectively preventing the cell from functioning or reproducing.

A number of such alkylating agents contain one or more aziridine rings or contain intermediate structures which can yield aziridine rings. An aziridine ring is a three-membered heterocyclic ring containing one nitrogen atom and two carbon atoms. Examples of alkylating chemicals which contain aziridine rings or contain structures which can yield aziridine rings are as follows:

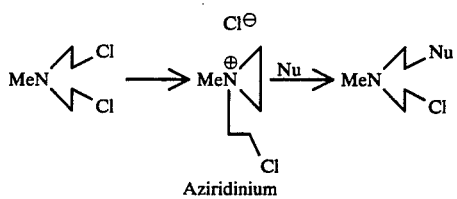

Mechanism of Nitrogen Mustard Alkylation

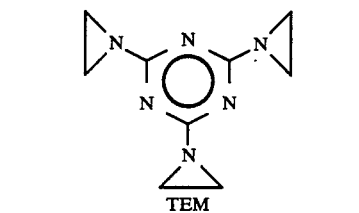

TEM

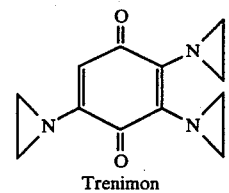

Trenimon

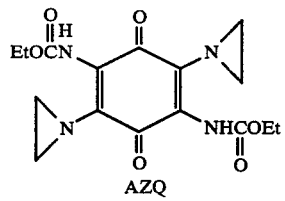

AZQ

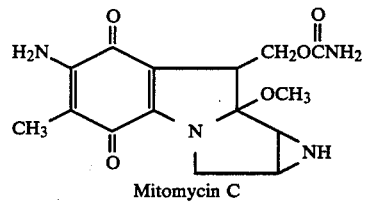

Mitomycin C

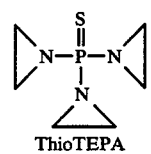

ThioTEPA

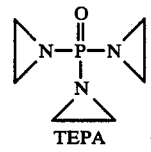

TEPA

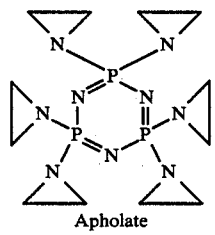

Apholate

-continued

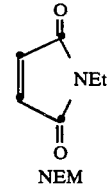

Cyclophosphamide

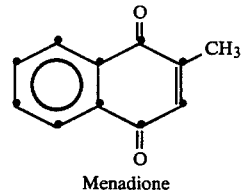

Phosphoramide Mustard

These compounds are believed to open at the aziridine ring site, if not already opened at that site, and then combine with a nucleic acid to interrupt the replication of the nucleic acid or to interfere with messages which would be transmitted by the nucleic acid.

In addition to the thio-TEPA and TEPA compounds, numerous other phosphoaziridines are known. Phosphoaziridines are described in numerous publications, for example, in U.S. Pat. No. 3,201,313; by Bardos et al in the Journal of Surgical Oncology 3(4): 431–441 (1971); by Kimler et al in Radiology, 133: pp 515–517 (1979); by Bardos et al in the International Journal of Radiation Oncology Biological Physics, Volume 5: pp 1653–1656 (1979); by Wampler et al in International Journal of Radiation Oncology Biological Physics, Volume 5: pp 1681–1683 (1979); and by Chmielewicz et al in the Journal of Pharmaceutical Sciences, Volume 56, No. 9: pp 1179–1181 (1967).

Initially, phosphoaziridines were considered and classified as alkylating agents. Such phosphoaziridines were later chemically combined through an amide linkage to ethyl carbamate in an attempt to obtain a synergistic effect between the phosphoaziridine and urethane group. The compound and many of its analogues demonstrate potent anti-tumor activity but showed no significant clinical advantage over other alkylating agents.

Bis(2,2-dimethyl-1-aziridinyl)phosphinates were subsequently developed which showed the interesting characteristic of not only being chemicals suitable for chemotherapy but demonstrated the ability to potentiate the therapeutic effects of radiation upon transplanted tumors. The Bis(2,2-dimethyl-1-aziridinyl)phosphinates which were connected with urethane groups or ester groups nevertheless show highly effective anti-tumor activity with remarkably low toxicity for inhibiting the production and development of blood cells (hematopoietic toxicity) when compared with conventional alkylating agents.

The radiation potentiating effect of the (2,2-dimethyl-1-aziridinyl)phosphinates is believed to operate by blocking repair of nucleic acid damaged by radiation; whereas, most other known radiation sensitizing compounds for hypoxic (anaerobic) tumors are believed to operate by increasing initial radiation damage to nucleic acids of the tumor. A useful group of such other known radio sensitizers are members of the "electron affinic" class of sensitizers. The structures of several of such known "electron affinic" anti-tumor radio sensitizers are shown below.

"Phosphoaziridines" as used herein include compounds wherein one to three aziridine rings are attached to a phosphorous atom and two valences of the phosphorous atom are connected to an oxygen or sulfur atom.

ELECTRON AFFINIC RADIATION SENSITIZERS

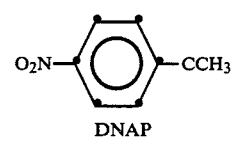

NEM

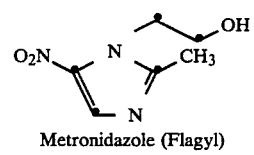

Menadione

DNAP

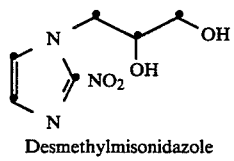

Metronidazole (Flagyl)

Misonidazole

Desmethylmisonidazole

Unfortunately, such electron affinic compounds which increase the radiation effect upon tumors are usually high neurotoxic.

BRIEF DESCRIPTION OF THE INVENTION

In accordance with the invention, there is provided a method for inhibiting the growth of tumor cells both by the direct effects of chemotherapy and by potentiating the effects of radiation upon the growth of the tumor. In accordance with the method, novel compounds of the invention are used both as a chemotherapeutic agent and as an electron affinic radiation sensitizer. In accordance with the method, tumor cells are exposed to an effective concentration of a compound of the invention usually in combination with radiation.

The compounds of the invention comprise at least two aziridine rings and have the formula:

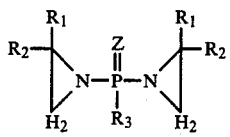

Z is oxygen or sulfur. $R_1$ is independently at each occurrence H or $-CH_3$. $R_2$ is independently at each occurrence $-CH_3$ or a nitro phenyl $R_5$ group. $R_3$ is $-N(R_4)_2$, $-OR_4$, $-SR_4$ or an aziridine radical having the formula:

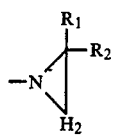

$R_4$ is a radical containing up to 30 atoms including at least one amine, ester, ether, alkyl, substituted alkyl, hydrogen, phenyl, substituted phenyl, carbamate, heterocyclic ring or $R_5$ group, provided that when $R_4$ contains an $R_5$ group, $R_4$ also contains at least one alkyl group between the phosphorus and the $R_5$ group. The presence of this alkyl group increases stability of the compound. $R_5$ is a radical containing an electron affinic group comprising a quinone or a heterocyclic or phenyl ring directly connected to a radical selected from the group consisting of nitro, nitroso, sulphonyl, sulfoxine and N-oxide. The compound must contain at least one $R_5$ radical and when $R_1$ is H, the $R_2$ group on the same ring is a nitro phenyl $R_5$. "Substituted" used herein means substituted with $-NO_2$, $-OH$, $-Cl$, $-F$, $-Br$, $-I$, $-SR_6$, $-N(R_6)_2$, $-OR_6$, $-COOR_6$, or $-COR_6$ where $R_6$ is alkyl or substituted alkyl. "Alkyl" as used herein is preferably alkyl of from 1 to 6 carbon atoms. "Nitrophenyl" includes mono and di nitro phenyl.

BEST MODE FOR CARRYING OUT THE INVENTION

As previously discussed, the method of the invention comprises the chemical inhibition of the growth of tumor cells and in addition comprises the potentiating of the effects of radiation upon such growth. In accordance with the method, tumor cells are exposed to radiation in conjunction an effective concentration of a compound of the formula:

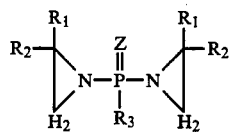

wherein Z; $R_1$; $R_2$; $R_3$; $R_4$; $R_5$; and $R_6$ are as previously described. The compound contains at least one $R_5$ radical and when $R_1$ is H, the $R_2$ group on the same ring is nitro phenyl $R_5$ group.

The effective concentration of the compound of the invention usually ranges between about 5 and 1500 milligrams per kilogram of body weight and is preferably about 10 and about 300 milligrams per kilogram of body weight of the organism being treated. The most common method of treatment is by intravenous injection. The radiation used can be relatively high or relatively low energy radiation ranging from X radiation to Gamma radiation from radioisotopes such as cobalt 60.

All of such radiation is of course considered high energy radiation when compared with the energy of radiation usually found in the natural environment. The radiation dose to the tumor site is usually between about 400 and about 5,000 rads over a time period from about 4 to about 60 minutes. After injection of the compound of the invention, sufficient time is permitted to allow the compound of the invention to collect at the tumor site. The time period from injection to exposure to radiation is usually from about 10 minutes to about 4 hours.

The organisms which are treated in accordance with the method of the invention are usually mammals including human beings.

In accordance with the method of the invention, the growth of tumor cells can be chemically inhibited, and in addition the effects of radiation upon cell growth within the tumor can be potentiated in a synergistic manner with chemical inhibition, with particular selectively toward hypoxic (anaerobic) cells which is desirable since many tumors are hypoxic. A more effective and selective toxicity to tumor cells (cytotoxic) and radio sensitizing action upon tumor cells may therefore be realized, possibly with lower doses of both chemotherapeutic agent and radiation and with the likelihood of more specific localized toxic effect at the tumor site so that decreased incidence of toxic side effects to the overall organism may be achieved.

Compounds of the invention containing unsymmetrical aziridine rings may be obtained by using intermediates containing aziridine rings having different substituents. When such methods are used, usually mixtures of compounds of the invention are obtained and isolation of the different specific compounds is usually difficult.

The compound of the invention therefore preferably contains aziridine rings wherein the $R_1$ and $R_2$ groups on one of the aziridine rings are the same as the $R_1$ and $R_2$ groups on the remaining aziridine rings. The compounds of the invention usually contain two aziridine rings but may contain as many as three aziridine rings since the $R_3$ group may itself be or contain an aziridine ring.

The compound of the invention also preferably contains an $R_5$ group which comprises a heterocyclic or phenyl ring directly connected to a nitro group at a 2 or 4 position of the $R_5$ ring where the $R_5$ is connected to the rest of the compound at the 1 position of the $R_5$ ring. Especially preferred compounds in accordance with the invention are those compounds wherein all $R_1$ and $R_2$ groups are methyl and the compound is therefore a Bis(2,2-dimethyl-1-aziridinyl)phosphinyl radical connected at the phosphorus atom, generally through intermediate linkages, to a $R_5$ group.

$R_3$ is commonly $-X-A-R_5$ where X is a radical selected from the group consisting of $-O-$, $-S-$, $-NH-$, $-NHCOO-$, $-NHCONH-$, $-NHCONHO-$, and $-NHCO-$. A is a substituted or unsubstituted alkyl group. In accordance with the present invention, $R_5$ is usually not quinone.

Intermediates for preparation of compounds in accordance with the present invention may be prepared in accordance with many methods known to those skilled in the art. General methods are disclosed in the references cited in Background Art. In general, $HR_3$ compounds (formula 1) can be attached to the phosphoryl moiety by reaction with $POCl_3$ or $Cl_2PONCO$ using the methods described in U.S. Pat. No. 3,201,313 in Bardos et al and in the previously discussed article by Chmielewicz et al which appeared in the Journal of Pharmaceutical Sciences, Volume 56, No. 9 September 1967 at pages 1179–1181. As a result of these reactions, intermediates of formula 2 are formed.

formula 2

In practice, the preferred acid acceptor in the reaction is triethylamine and the solvents of choice are toluene, tetrahydrofuran, ether or 1,2-dimethoxyethane. Essentially any anhydrous inert solvent of appropriate purity can however be used.

Intermediates of formula 2 are then reacted with an aziridine intermediate of formula 3.

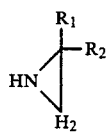

formula 3

The reaction takes place at the appropriate molar ratio so that the aziridine groups become attached to the phosphorus atom to form the compounds of the invention. If $HR_3$ is similarly an aziridine, the reaction of the aziridines with $POCl_3$ may take place in a one-step operation.

Intermediates of formula 3 may be prepared by methods known to those skilled in the art. Examples of such preparations are the Wenker and Gabriel syntheses. The Wenker synthesis is described in the Journal of the American Chemical Society, Volume 57 at 2328 (1935) and the Gabriel synthesis is described in Ber. Volume 21 at 1049 (1888).

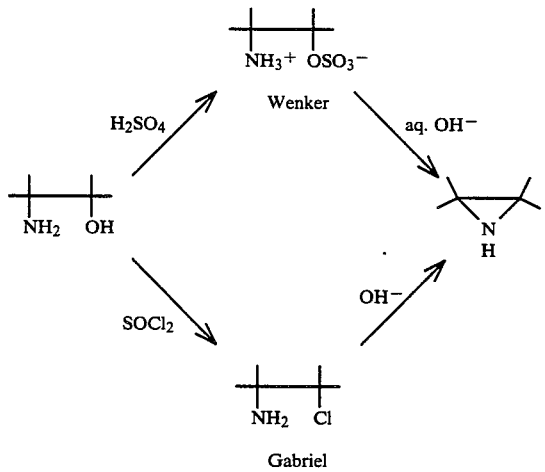

Other methods for preparation of intermediates of formula 3 are described by Derm et al in "Ethyleneimine And Other Aziridines" Academic Press, New York, 1969. A general review of methods of synthesis of intermediates of formula 3 is given by Michael Ellis Perlman, an inventor herein, in a State University of New York thesis entitled "Synthesis And Mechanistic Studies Of Phosphoraziridines As Radiation Sensitizers" the abstract of which is to be first published in May of 1982.

A particularly interesting synthesis of compounds of formula 3 is as follows:

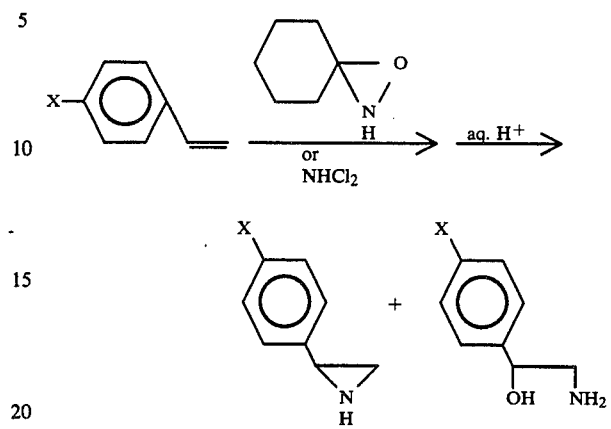

X may be an electron affinic radical such as a nitro group.

Intermediates of formula 1, i.e. $HR_3$ can be prepared by many methods known to those skilled in the art. Many of such prior art methods are reviewed by Michael Ellis Perlman in the thesis previously discussed.

Specific preparations of compounds in accordance with the present invention are now set forth. The following examples serve to illustrate and not limit the present invention.

EXAMPLE I

Preparation of ethyl Bis(2-(p-nitrophenyl)aziridinyl)phosphinate

An equation showing structural formulas for the preparation of ethyl bis(2-(p-nitrophenyl)-1-aziridinyl)phosphinate (formula 4) is set forth below.

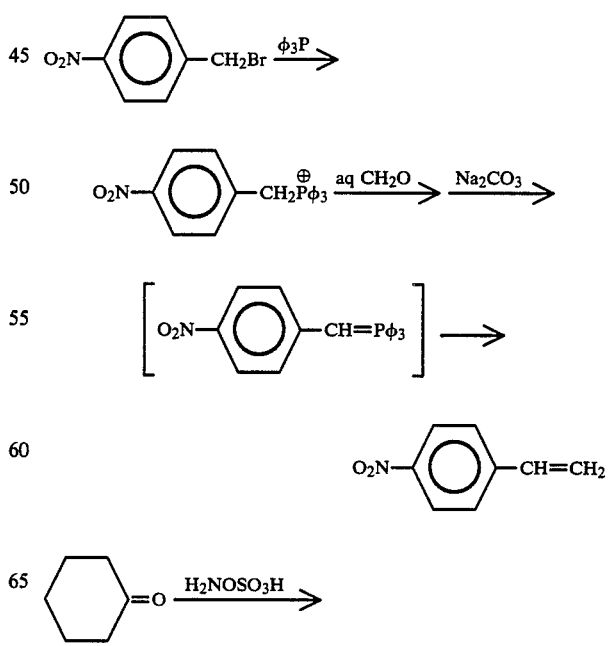

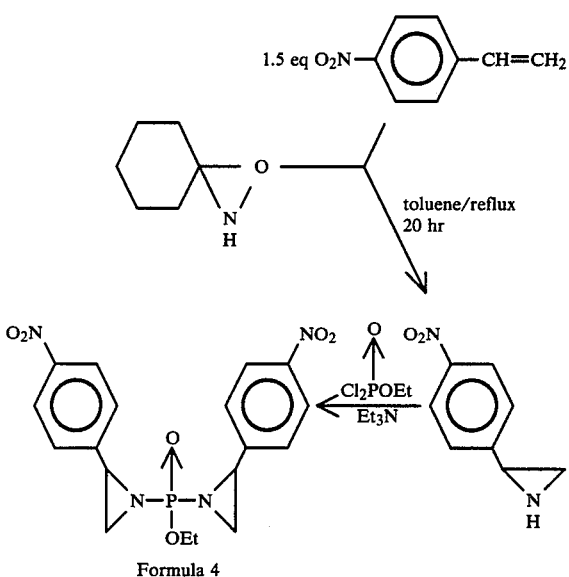

Formula 4

Specific examples leading to the preparation of formula 4 are as follows:

p-Nitrobenzyl phosphonium bromide p-Nitrobenzylbromide (54.0 g, 0.25 mol) and triphenylphosphine (65.6 g, 0.25 mol) were dissolved in 150 mL of dry benzene in a flask equipped with a drying tube. The solution was heated on a steam bath with swirling until a majority of product had precipitated (5 min), and then was allowed to cool to near ambient temperature with occasional agitation. Filtration of the precipitate and washing with 3×200 mL anhydrous ether yielded 100.8 g of the desired product as an off-white powder. The filtrate was flash evaporated to 50 mL and heated on a steam bath for 5 min, then chilled overnight to provide an additional 11.4 g of product (93.8% yield).

p-Nitrostyrene

The above prepared phosphonium salt (112 g, 0.234 mol) was suspended in 450 mL 37% aqueous formaldehyde. 150 mL of 1M $Na_2CO_3$ solution was added in small portions over 25 min with vigorous stirring, waiting until the deep red color had dissipated before each addition. The suspension was stirred for another 3¼ h, then the pale yellow oil was separated and the aqueous layer was extracted three times with 175 mL 1,2-dichloroethane. The organic extracts were combined with the oil, dried over anhydrous sodium sulfate, and flash evaporated to 131 g of oil. Chromatography on 1 kg neutral alumina (Fisher Activity Grade 111) with light petroleum ether as eluent provided 33.4 g (95.7%) of p-Nitrostyrene as a yellow oil with just trace impurities indicated by NMR.

3,3-Pentamethyleneoxaziridine

A mixture of cyclohexanone (18.63 mL, 17.64 g. 0.18 mol) in 315 mL toluene and 90 mL 2N NaOH was cooled to 2° C. A cold, freshly prepared solution of hydroxylamine-O-sulfonic acid (20.7 g. 0.18 mol) in 180 mL water and 90 mL 2N NaOH was added and the temperature rose to 5° C. The mixture was then vigorously stirred for 10 min, maintaining the temperature at 6° to 10° C., with an ice bath. The organic (upper) layer was immediately separated and then dried with anhydrous sodium sulfate in the cold overnight. Filtration and flash evaporation at 30° C. provided 170 mL of very pale yellow solution of the desired product.

The concentration of oxaziridine was determined by iodometric titration: 10 mL glacial acetic acid was added to 1.25 mL of oxaziridine solution, followed by 2 mL of 5% potassium iodide solution. The mixture was immediately agitated and the resulting brown mixture titrated with 0.100N sodium thiosulfate solution until clear. Based on the consumption of 2 moles $S_2O_3^{-2}$ for each mole oxaziridine, the concentration of oxaziridine was found to be 0.290M (27.4% yield).

2-(p-Nitrophenyl)aziridine p-Nitrostyrene (7.49 g, 0.0502 mol) and 3,3-Pentamethylene oxaziridine (115.5 mL, 0.355 mol) in toluene solution were refluxed for 20 h. After being allowed to stand at room temperature, the solution was decanted from tar and flash evaporated to 11.4 g of thin brown oil. This was chromatographed on 160 silical gel (Baker) packed in 1% petroleum ether in 1,2-dichloroethane. The product was eluted with 0.5% MeOH in dichloroethane and was obtained as 2.876 g of orange powder that was mostly aziridine by TLC (Eastman alumina, dichloroethane) (crude yield 52.6%). Recrystallization from ether with extensive treatment with Norit yielded 0.511 g (9.3%) of product as tan crystals: mp 69°-72.5° C.; TLC(ether) gave a spectrum essentially identical to the published spectrum.

Ethyl Bis(2-(p-nitrophenyl)-1-aziridinyl)phosphinate

Ethyl phosphorodichloridate (0.407 g, 2.5 mmol) in 5 mL dry toluene was added dropwise over 20 min to 2-(p-nitrophenyl)aziridine (0.816 g, 5.0 mmol) and triethylamine (0.526 g, 0.725 mL, 5.2 mmol) in 20 mL toluene at −2° C. with stirring. The suspension was subsequently stirred at 4° C. for 23 h and then at room temperature for 5 h. The precipitate was filtered and washed with 40 mL toluene to yield 0.648 g Et₃N.HCl (94.2%). The filtration was flash evaporated at 35° C. to an amber glass (1.15 g). This was applied to thick layer silica gel plates that were developed with dry THF. The major short UV absorbing band from each plate was extracted with 3×20 mL 1,2-dichloroethane/MeOH (5:1). The extracts were flash evaporated, taken up into 25 mL methylene chloride and filtered. Removal of the solvent yielded 0.789 g of yellow, viscous oil. Trituration with ether and cooling afforded 0.634 g of off-white powder, which was recrystallized from THF/hexanes to give 0.492 g (47.0%) of the desired product (formula 4) as a powder.

EXAMPLE II

Preparation of p-nitrobenzyl Bis(2,2-dimethyl-1-aziridinyl)phosphinyl carbamate (formula 5)

An equation, showing structural formulas, for the preparation of formula 5 is as follows:

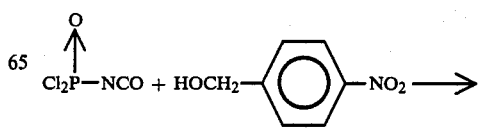

11

-continued

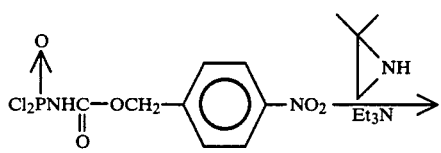

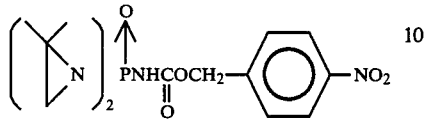

Formula 5

Specific preperations leading to the synthesis of p-nitrobenzyl Bis(2,2-dimethyl-1-aziridinyl)phosphinyl carbamate are as follows:

p-Nitrobenzyl Dichlorophosphinyl Carbamate p-Nitrobenzyl alcohol (0.459 g, 3.0 mmol) in 2 mL dry THF was added dropwise over 20 min to dichloroisocyanatophosphine oxide (0.504 g, 3.03 mmol) in 3 mL THF at 0° C. with stirring. The solution was stirred for another 45 min at 0° C., allowed to reach room temperature and was used immediately in the next step.

p-Nitrobenzyl Bis(2,2-dimethyl-1-aziridinyl)phosphinyl Carbamate

The above solution of p-nitrobenzyl dichlorophosphinyl carbamate was added dropwise over 20 min to 2,2-dimethylaziridine (0.427 g, 6.0 mmol) and triethylamine (0.837 mL, 0.607 g. 6.0 mmol) in 2 mL dry THF at −2° C. with stirring. The suspension was then stirred at 4° C. for 20 h and filtered. The residual powder was washed with 3×5 mL cold THF to yield 1.205 g. It was then washed with 15 mL THF at ambient temperature to provide 0.820 g Et₃N.HCl (Calcd. wt. 0.826 g, 99.3%). The THF washings were flash evaporated to a white powder, which was recrystallized from THF/hexanes to yield 0.637 g (55.5%) of the desired p-Nitrobenzyl Bis(2,2-dimethyl-1-aziridinyl)phosphinyl carbamate, i.e. formula 5, as white plate-clusters.

EXAMPLE III

2-(2-Nitro-1-imidazoyl)ethyl Bis(2,2-dimethyl-1-aziridinyl)phosphinyl carbamate Equations, showing structural formulas, leading to the preparation of 2-(2-nitro-1-imidazoyl)ethyl bis(2,2-dimethyl-1-aziridinyl)phosphinyl carbamate, formula 6, are as follows:

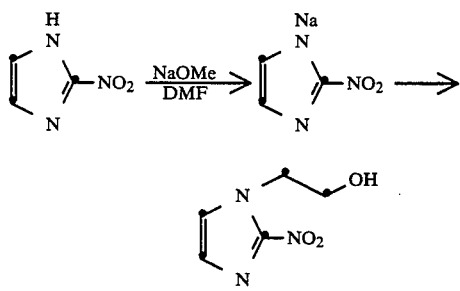

12

-continued

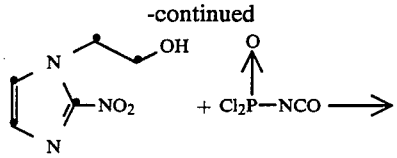

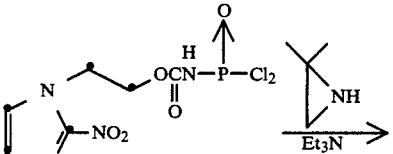

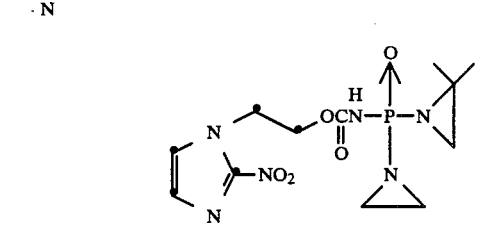

Formula 6

Specific preparations leading to the synthesis of 2-(2-nitro-1-imidazoyl)ethyl Bis(2,2-dimethyl-1-aziridinyl)-phosphinyl carbamate (formula 6) are as follows:

2-(2-Nitro-1-imidazoyl)ethanol

To a suspension of 2-nitroimidazole (4.00 g, 35.4 mmol) in 40 mL dry DMF was added dropwise 3N NaOMe in MeOH until the imidazole had dissolved completely and the solution had just turned red. Further imidazole was added until the color just returned to yellow. The MeOH was then removed by heating to 110° C., removing the condenser, and continuing heating up to a bath temperature of 152° C. After cooling the solution to 110° C., 2-bromoethanol (2.74 mL, 4.82 g, 38.6 mmol, Aldrich, redistilled) was added and the bath temperature maintained at 110° C. for 1-½ h. The yellow solution was then flash-evaporated at 40° C., under a high vacuum until a yellow paste was obtained. This was subsequently extracted five times with 20 mL acetone and the acetone solutions evaporated to a yellow solid, which was treated with 25 mL EtOAc and the solvent again evaporated. The resulting material was extracted with 10 mL saturated Na₂CO₃, twice with 20 mL half-saturated Na₂CO₃, and finally twice with 10 mL water. The remaining crystalline material, 2.96 g, was free of 2-nitroimidazole by TLC (Eastman silica gel, DME). The aqueous solutions were extracted twice with 25 mL EtOAc, and the organic layers then washed with 5 mL half-saturated Na₂CO₃, 5 mL water, and then dried over anhydrous MgSO₄. Concentration to 20 mL and cooling yielded 0.586 g of product, mp 112°–116.5° C. The two crystalline products were recrystallized from EtOH to yield 1.92 g (34.5%) of the desired 2-(2-Nitro-1-imidazoyl)ethanol as yellow-green needles.

2-(2-Nitro-1-imidazoyl)ethyl Dichlorophosphinyl Carbamate 2-(2-Nitro-1-imidazoyl)ethanol) (0.943 g, 6.0 mmol) in 40 ml dry THF was added dropwise under N₂ to dichloroisocyanatophosphine oxide (0.975 g, 0.602 mL) in 20 mL THF over 2-¼ h at 0°–2° C. After stirring for an additional 30 min with the cooling bath removed, TLC indicated that a trace of alcohol remained. Consequently, an additional 0.03 mL of the phosphine oxide was added and stirring continued at room temperature for 30 min to bring the reaction to completion. The resulting solution was used immediately in the next step.

2-(2-Nitro-1-imidazoyl)ethyl Bis(2,2-dimethyl-1-aziridinyl)phosphinyl Carbamate (formula 6)

The above solution of 2-(2-Nitro-1-imidazoyl)ethyl Dichlorophosphinyl Carbamate was added dropwise over 60 min to 2,2-dimethyl-aziridine (0.853 g, 1.084 mL, 12 mmol) and triethylamine (1.215 g, 1.68 mL, 12 mmol) in 40 mL dry THF at $-4°$ to $-2°$ C. with stirring under $N_2$. After stirring for 19 h at 4° C., another 0.05 mL aziridine (0.6 mmol) and 0.08 mL triethylamine (0.6 mmol) were added and the reaction and stirred for another 3½ h at 4° C. to achieve completion, according to TLC analysis. Filtration of the suspension and washing of the residual powder with 40 mL cold THF yielded 1.577 g of $Et_3N.HCl$ (Calcd. wt. 1.653 g, 95.4%). The filtrate was rotary evaporated to a yellow resin, which was dissolved in 20 mL THF, a few mL hexane added and THF flash evaporated off until crystallization was initiated. Subsequent cooling provided 0.993 g (42.8%) of the desired product of formula 6 as a pale yellow powder.

EXAMPLE IV 2-(2-nitro-1-imidazoyl)ethyl Bis(2,2-dimethyl-1-aziridinyl) phosphinate A solution of 3.0 mmol of 2-(2-nitro-1-imidazoyl)ethanol in 17 ml dry THF is added dropwise over 1 hr to 7.0 mmol phosphorus oxychloride in 5 ml THF at $-7°$ to $-2°$ C. with stirring. The suspension is stirred for another 75 min at 0° C., then allowed to reach room temperature and filtered. The residual powder is washed under a nitrogen flow with THF and the solvent and excess $POCl_3$ removed from the filtrate in vacuo over 1 hr to yield 2-(2-nitro-1-imidazoyl)ethyl phosphorodichloridate as an oil.

A solution of the dichloridate in 10 ml THF is added dropwise over 15 min to 6.2 mmol 2,2-dimethylaziridine and 7.0 mmol triethylamine in 10 ml THF at $-7°$ to $-4°$ C. with stirring. The suspension is stirred for another 19 hr at 4° C., allowed to reach room temperature and filtered. The residual powder is washed with THF and filtrate flash evaporated to an oil. Chromatography on silica gel thin layer plates using THF containing 3% $Et_3N$ as the developing solvent is performed. The product is extracted out and dry 2,2-dimethyl-1-aziridinyl phosphinate is obtained as an oil.

EXAMPLE V o-Nitrobenzyl Bis(2,2-dimethyl-1-aziridinyl)phosphinyl Carbamate

A solution of 6.0 mmol of o-nitrobenzyl alcohol in 15 ml dry THF is added over a period of 70 min to 6.0 mmol dichloroisocyanatophosphine oxide in 15 ml THF at 0° C. with stirring. The resulting solution of o-nitrobenzyl dichlorophosphinyl carbamate is allowed to reach room temperature. It is then added dropwise over 40 min at $-2°$ to 0° C. to a solution of 13.0 mmol 2,2-dimethylaziridine and 13.0 mmol triethylamine in 20 ml THF. After stirring at 4° C. for 18 hr the precipitated salt is removed by filtration and washed with 50 ml THF. The filtrate is flash evaporated to dryness. Recrystallized from THF-hexane yields 1.66 g of o-nitrobenzyl bis(2,2-dimethyl-1-aziridinyl)phosphinyl carbamate, m.p.=123°–135° C.

EXAMPLE VI

The composition of matter described in Example III, i.e., 2-(2-nitro-1-imidazoyl)-ethyl bis(2,2-dimethyl-1-aziridinyl)phosphinyl carbamate, abbreviated herein as NIEDAPC, was tested for antitumor activity in vivo using the lymphocytic leukemia P-388 in mice, the test system employed by the NCI for the primary screening of antitumor agents, according to Protocol 1.200 (Cancer Chemo. Rpts. Part 3, Vol. 3, No. 2, p. 9; 1972). In the study, $10^6$ ascites cells were implanted in the peritoneal cavity of CDF female mice. The drug was given in a single injection, on Day 1 only, at six dose levels (6×4 mice). The control animals receives saline (10 mice). Test criteria (according to NCI protocol): Toxicity is indicated where <4/6 or <¾ mice are alive on Day 5. Antitumor activity is indicated where % T/C≧125, where % T/C=(MST treated/MST control)×100, and MST=medium survival time. The results are shown in Table 1.

The results for NIEDAPC are shown in the following Table:

TABLE 1

| Material | Dose, IP mg/kg/inj | MST Days | Effect MST % T/C | AWC gm d.6 |
|---|---|---|---|---|
| NIEDPAC (in $H_2O$) | 256 | 13.5 | 169 | −1.0 |
| | 128 | 12.5 | 156 | −1.1 |
| | 64 | 11.5 | 144 | −0.5 |
| | 32 | 10.0 | 125 | +0.8 |
| | 16 | 10.0 | 125 | +0.6 |
| | 8 | 9.0 | 113 | +1.6 |
| Control | Saline | 8.0 | — | — |

Tumor inoculum is $10^6$ ascites cells implanted i.p.
Host is $CDF_1$ mice
Treatment is for Day 1 only
Toxicity shown when <4/6 or <¾ mice alive on Day 5; average weight change on Day 6.
MST is median survival time
% T/C is (MST treated/MST control) × 100
% T/C ≧ 125 is considered significant antitumor activity
Conclusion: The drug has significant antitumor activity in this in vivo test system even without X-irradiation.
The electron affinic sensitizer misonidazole shows no activity in this test system.

EXAMPLE VII

The effect of NIEDAPC on the radiation sensitivity of irradiated hypoxic mammalian cells, was studied essentially according to the method of Kimler et al., (Radiology, 133, 515; 1979).

The results demonstrate that the exposure of V-79 tumor cells to $5.0 \times 10^{-4}M$ concentration of NIEDAPC for 1 hr, significantly reduces the resistance of the subsequently washed cells to X-irradiation, under hypoxic conditions. In fact, the activity of NIEDAPC in this system is comparable to that of misonidazole, the prototype electron-affinic sensitizer. Phosphoraziridines, other than those of this invention, do not have this type of activity.

It is to be understood that the foregoing examples are not intended to limit the invention and that many $R_1$, $R_2$ and $R_3$ groups can be substituted in the intermediates and resulting compounds. It is further to be understood that sulfur can often be substituted as the Z group in both the intermediate and final compounds in the syntheses shown.

EXAMPLE VIII

All of the phosphorus containing aziridine compounds prepared in accordance with the previous examples are tested against *staphylococcus aureaus, clostridium perfringens,* and *Actinomyces viscosis* in a tube dilution test. Most of such compounds are found to have at least some antimicrobial activity.

What is claimed is:

1. A compound of the formula:

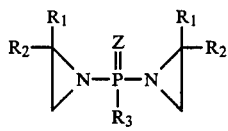

wherein Z is oxygen or sulfur, $R_1$ is hydrogen or methyl; $R_2$ is methyl or nitrophenyl; $R_3$ is

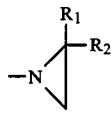

or lower alkoxy or lower alkoxy substituted by nitro-1-imidazoyl, quinone, or nitrophenyl or $R_3$ is —NH-COOR$_4$ wherein $R_4$ is lower alkyl substituted by nitrophenyl, nitro-1-imidazoyl or quinone; with the proviso that the compound must have at least one nitrophenyl, nitro-1-imidazoyl or quinone and when $R_4$ is nitrophenyl substituted methyl, the nitrophenyl is O-nitrophenyl.

2. A compound of the formula:

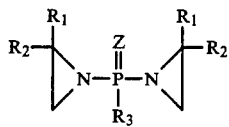

wherein Z is oxygen or sulfur, $R_1$ is hydrogen or methyl; $R_2$ is methyl or nitrophenyl; $R_3$ is

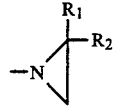

or lower alkoxy or lower alkoxy substituted by nitro-1-imidazoyl, quinone or nitrophenyl or $R_3$ is —NH-COOR$_4$ wherein $R_4$ is lower alkyl substituted by nitro-1-imidazoyl or quinone; with the proviso that the compound must have at least one nitrophenyl, nitro-1-imidazoyl or quinone.

3. The compound of claim 1 wherein the $R_1$ and $R_2$ groups on one of the aziridine rings are the same as the $R_1$ and $R_2$ groups on the remaining aziridine rings.

4. The compound of claim 1 wherein the compound is p-Nitrobenzyl bis(2,2-dimethyl-1-aziridinyl)phosphinyl carbamate.

5. The compound of claim 1 wherein the compound is 2-(2-nitro-1-imidazoyl)-ethyl bis(2,2-dimethyl-1-aziridinyl)phosphinyl carbamate.

6. The compound of claim 1 wherein the compound is 2-(2-nitro-1-imidazoyl)ethyl bis(2,2-dimethyl-1-aziridinyl)phosphinate.

7. The compound of claim 1 wherein the compound is o-nitrobenzyl bis(2,2-dimethyl-1-aziridinyl)phosphinyl carbamate.

8. The compound of claim 1 wherein the compound is ethyl bis(2-(p-nitrophenyl)aziridinyl)phosphinate.

* * * * *